United States Patent [19]

Bauer

[11] 4,391,905

[45] Jul. 5, 1983

[54] SYSTEM FOR THE DETERMINATION OF GLUCOSE IN FLUIDS

[75] Inventor: Robert Bauer, Bristol, Ind.

[73] Assignee: Miles Laboratories, Inc., Elkhart, Ind.

[21] Appl. No.: 358,266

[22] Filed: Mar. 15, 1982

Related U.S. Application Data

[62] Division of Ser. No. 233,928, Feb. 12, 1981, Pat. No. 4,340,669.

[51] Int. Cl.³ .......................... G01N 33/50; C12Q 1/54
[52] U.S. Cl. ........................................ 435/14; 422/56; 435/25; 435/28; 435/805; 435/810; 436/95
[58] Field of Search ...................... 436/95; 435/14, 25, 435/28, 805, 810; 422/56, 57; 427/2, 3

[56] References Cited

U.S. PATENT DOCUMENTS

| | | | |
|---|---|---|---|
| 3,008,879 | 11/1961 | Harvill | 422/54 X |
| 3,411,887 | 11/1968 | Ku | 422/57 X |
| 3,630,847 | 12/1971 | Rey et al. | 435/14 |
| 3,814,668 | 6/1974 | Blake et al. | 435/14 |
| 3,964,870 | 6/1976 | Tiedemann et al. | 435/14 |
| 4,148,611 | 4/1979 | Nand et al. | 422/56 X |
| 4,260,679 | 4/1981 | Tsuda et al. | 435/14 X |
| 4,278,439 | 7/1981 | White | 23/901 X |
| 4,279,993 | 7/1981 | Magers et al. | 435/14 |

FOREIGN PATENT DOCUMENTS 1464359 2/1977 United Kingdom .

OTHER PUBLICATIONS

Chem. Abstracts 75: 104852 U; 1971; Stamatova et al.
Dolmanova, I. F. et al. Vestn. Mosk. Univ., Khim 1970, 11(5), 573-577.
Krause, F., Oesterr. Chem.-Ztg. 68(2), 54-55(1967).

Primary Examiner—Kenneth M. Schor
Attorney, Agent, or Firm—Jerome L. Jeffers

[57] ABSTRACT

The present invention involves an improved test system for the determination of glucose in aqueous fluids of the type which comprises glucose oxidase, a peroxidatively active substance and chromogen. The improvement involves the use of m-anisidine as a chromogen which permits the semi-quantitative determination of glucose at higher concentrations than is possible with previously used chromogens.

5 Claims, No Drawings

SYSTEM FOR THE DETERMINATION OF GLUCOSE IN FLUIDS

This application is a division of application Ser. No. 233,928, filed Feb. 12, 1981, now U.S. Pat. No. 4,340,669.

BACKGROUND OF THE INVENTION

The present invention is concerned with a process for the semi-quantitative determination of the presence of high levels of glucose in aqueous fluids and with a particular indicator (chromogen) useful in such determination.

The determination of glucose in body fluids, such as urine or blood, is of importance not only in the case of diabetic patients who must control their sugar input, but it is also important in those situations in which the detection of disease as a public health measure requires the screening of the urine or blood of large numbers of people. Because early diagnosis and continued control are so important in diabetes, a glucose test, to be of greatest value to the physician in his diagnosis and control of the disease, must be conveniently rapid, simple enough to serve the clinician and sensitive enough to reflect meaningful variations in urine or blood glucose.

The use of glucose oxidase, a peroxidatively active substance and a chromogen, which is oxidized upon exposure to hydrogen peroxide in the presence of the peroxidatively active substance, for the detection of glucose in urine is known. The system involves the formation of hydrogen peroxide by the action of glucose oxidase on glucose:

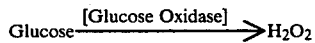

and the resultant oxidation of the chromogen (Cr) to its oxidized state (Cr*) which is visually detectable by a color change:

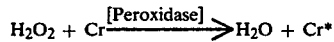

The test described above can be used in the determination of a series of materials which react with oxygen and an oxidase resulting in the formation of hydrogen peroxide. Thus, the system is useful for the detection of occult blood in various body tissues because of the fact that hemoglobin is such a material. Several different chromogens have been reported as being useful in the determination method under consideration. U.S. Pat. No. 3,012,976 discloses the use of o-tolidine, o-toluidine, p-toluidine, o-phenylenediamine, N,N'-dimethyl-p-phenylene-diamine, N,N'-diethyl-p-phenylenediamine, benzidine, p-anisidine, o-catechol and pyrogallol in an occult blood test of the type under consideration. U.S. Pat. No. 3,335,069 involves a test for uric acid and describes the use of o-anisidine and p-anisidine as chromogens.

Of the chromogens disclosed as being useful, few have been actually used in practice. Benzidine was a preferred chromogen, but due to the discovery that it is a potent carcinogen, it lost favor. The discovery that 3,3',5,5'-tetraalkylbenzidines were not carcinogens and the publication of this discovery, led to the obvious expedient of using one of these compounds as the chromogen in a system of the type described above. Such is disclosed in British Patent Specification No. 1,464,359.

Page 5 of this specification discloses the observed results with o-tolidine, tetramethylbenzidine and tetraethylbenzidine as chromogen at 0, 50, 100, 250, 500 and 1,000 milligram (mg.) % glucose in the fluid being tested. Each of these materials turns from yellow to bright green when the concentration of glucose increases from 0 to 50 mg. %. As the concentration of glucose increases the color of the oxidized chromogen darkens so that the observed colors were olive-black, black and deep green, respectively. This observation highlights a problem with the semi-quantitative determination of glucose in aqueous fluids because at higher concentrations, known chromogens appear black or very dark green thereby limiting their utility as chromogens in semi-quantitative test devices. Semi-quantitative determination of glucose in urine when the glucose concentration is high, i.e., from about 2,000 to 5,000 mg. % is especially important because urine glucose concentrations in diabetic patients can be as high as 5% or higher. The quantitative estimation of urine glucose to concentrations of 5% is important for at least two reasons: (a) High urine glucose concentrations are likely to be associated with diabetic coma. In emergency situations, it is important to determine whether a state of unconsciousness is diabetic coma. A stat test of this description, indicating a high urine glocuse concentration would therefore suggest diabetic coma, (b) Urine glucose levels become elevated if an insufficient amount of insulin has been administered. A test which can estimate high urine glucose concentrations therefore has greater utility in the therapeutic monitoring of insulin requirements.

The use of m-anisidine as a chromogen in reactions involving peroxides and peroxidase is not reported in the literature. Two references report the use of m-anisidine in systems containing peroxide and trace amounts of $Cu^{++}$. They are:

Dolmanova, I. F., et al., "Mechanism of the Catalytic Action of Copper in the Oxidation of a Series of Organic Compounds by Hydrogen Peroxide". Vestn. Mosk, Univ., Khim 1970, 11 (5), 573.

Krause, F., "Organic Inhibitors Which are Converted Into Active Redox Catalysts by Trace Amounts of $Cu^{++}$". Oesterr. Chem. Ztg. 68 (2), 54 (1967).

It would be desirable, and it is an object of the present invention to provide an improved method for the detection of glucose in aqueous fluids by the glucose oxidase/peroxidatively active substance system, which method is useful for the semi-quantitative determination of glucose at concentrations of 2000 to 5000 mg. %.

SUMMARY OF THE INVENTION

The present invention is an improvement to a test composition for the determination of the presence of glucose in a liquid test sample. The test composition, which comprises glucose oxidase, a peroxidatively active substance and a chromogen reactive with hydrogen peroxide which reaction is catalyzed by the peroxidatively active substance, is improved by the use of m-anisidine as chromogen.

DETAILED DESCRIPTION AND PREFERRED EMBODIMENTS

For the purpose of this application the term "fluids" shall be understood to refer to body fluids, such as blood serum, blood plasma, urine, spinal fluids and, in addition, shall refer to aqueous solutions containing urea. Although the most preferred application of the test means and process of this invention is to body fluids, such as blood and urine, it should be understood that the disclosed test means and process can be applied to industrial fluids as well.

The glucose indicator of the invention can be in the form of a treated paper, a bottled reagent, a frangible capsule containing the indicator in reagent form, a pill or tablet which can be dropped into water or alcohol or the fluid being tested for glucose, or a solid alcohol gel containing the reagent. When in pill or tablet form the indicator may contain a heat-generating substance, such as lithium chloride, which provides heat when placed in water, thus accelerating the reaction rate.

The preferred glucose indicator is prepared by treating a suitable carrier matrix with glucose indicator composition in the form of liquid reagent. Th expression "carrier matrix" refers to either bibulous or nonbibulous matrices which are insoluble in and maintain their structural integrity when exposed to water or other physiological fluids. Suitable bibulous matrices which can be used include paper, cellulose, wood, synthetic resin fleeces, woven and nonwoven fabrics and the like. Nonbibulous matrices include glass fiber and organo-plastic materials, such as polypropylene and the like. The carrier matrix can be soaked, immersed in, sprayed or printed with the liquid reagent composition and the carrier matrix thereafter dried by suitable means, such as ambient or forced air drying to leave the dry reagent-/matrix combination. The matrix can advantageously be affixed to an insoluble support member such as an organoplastic strip, e.g., polystyrene, by suitable means, such as double faced adhesive tape, for ease of use.

A typical liquid reagent composition will contain from 1,000 to 1,600 international units (I.U.) of glucose oxidase per ml., 600 to 1,300 I.U. of horseradish peroxidase per ml., and from 10 to 15 milligrams/ml. of m-anisidine as chromogen. In a preferred embodiment, a small amount, 0.5 to 1.0 milligram/ml., of a second indicator having a high extinction coefficient is employed. This is the case because test systems of the type under consideration using m-anisidine as chromogen give semi-quantitative readings over the range of 250 to 5,000 mg. per deciliter (mg./dl.) with color breaks at about 250, 500, 1,000, 2,000 and 5,000 mg./dl. The addition of a small amount of a second chromogen having a high extinction coefficient provides a system which is capable of detecting the presence of glucose in smaller concentrations, e.g., 100 mg./dl., while possessing the ability to differentiate between concentrations of 2,000 and 5,000 mg./dl. which levels are normally difficult, if not impossible, to distinguish.

Suitable materials for use as the second chromogen include o-tolidine, benzidine, syringaldazine, diaminofluorine and tetramethylbenzidine. Preferably tetramethylbenzidine is added to provide semi-quantitative sensitivity at low glucose concentrations. Since the glucose determination works best at a pH of from about 5.0 to 7.0, a buffer is normally added to the composition to maintain the desired pH.

Substances having peroxidative activity which are useful in the present invention can be chosen from various organic and inorganic sources. Plant peroxidases, such as horseradish peroxidase or potato peroxidase, can be used. Inorganic compounds having peroxidase activity include iodides, such as sodium and ammonium iodides, and molybdates, such as potassium and ammonium molybdates. In addition, urohemin and a number of other prophyrin substances having peroxidative activity can be used. Other substances which are not enzymes, but which have peroxidative activity include such compounds as iron sulfocyanate, iron tannate, ferrous ferrocyanide, potassium chromic sulfate and the like.

The invention is further illustrated by the following examples:

EXAMPLE I

An experiment was carried out to demonstrate the improvement in quantification achieved with the use of the indicator m-anisidine in the above described test device. The experiment was limited to show the improvement with glucose concentrations of from 2,000 to 5,000 (mg./dl.). While the units used in this example are mg./dl. it should be noted that they are equivalent to the mg. % used in the prior art. Strips were prepared from test solutions by impregnating Whatman 31 ET paper with the liquid reagent composition and drying the treated paper at 50° C. for 15 minutes.

Several test solutions were prepared using the following general formula:

| | |
|---|---|
| Citrate buffer, 2.0 M, pH 5.5 | 1.0 ml. |
| Peroxidase (Horseradish), 50 milligrams per milliliter (mg./ml.) | 2.0 ml. |
| Glucose Oxidase (5,000 I.U./ml.) | 3.0 ml.* |
| Polyvinyl Pyrrolidone (15% in ethanol) | 1.9 ml. |
| Emulphor ON-870, 10% ethanol | 0.5 ml. |
| Indicator | 0.001 mole |
| Tetrahydrofuran | 1.6 ml. |
| Total volume | 10.0 ml. |

*Lesser amounts of glucose oxidase were used with certain indicators. Water was added in these cases to bring the total volume to 10 ml.

Emulphor ON-870 is a nonionic detergent. Its purpose is to provide better strip wettability which, in turn, provides more uniform color development.

The number of glucose oxidase units added was varied to meet the needs of each indicator. The room temperature incubation times for the resulting strips were, therefore, varied only between 60 and 90 seconds. The amounts of glucose oxidase were varied to allow each system to develop approximately the same amounts of color at any given incubation time. Therefore, those systems using indicators with lower molar extinction coefficients contained correspondingly higher glucose oxidase concentrations. This is normally what is done to optimize the quantitation of a test strip composition. If the glucose oxidase concentration was held the same for all indicators, strips using indicators with higher extinction coefficients might develop colors so dark in response to 2% glucose that the 2% and 5% glucose concentrations might not be distinguishable.

Reflectance measurements were taken at the optimum wavelength for each indicator after dipping the strips in either 2,000 or 5,000 mg./dl. glucose in urine. The percent reflectance values for the two glucose concentrations were converted to KS values. Reflectance measurements can be converted to K/S values by the following formula:

$$K/S = (1-R)^2/2R$$

where K is the absorption coefficient of the sample, S is the light-scattering coefficient of the matrix, and R is the fraction of incident light reflected from the reagent pad. This is a simplified version of the Kubelka-Munk equation. K/S values are related to reflectance measurements as absorbance is to transmittance measurements. These plots (K/S vs. % glucose) provide a more equitable comparison of indicators having different molar extinction coefficients. A plot of K/S values vs. glucose concentrations of 2,000 and 5,000 mg./dl. gave slopes which provided a measure of quantitative capabilities of each indicator. The following table lists the calculated and normalized values for the slopes obtained.

| Indicator | Slope | Normalized Value |
| --- | --- | --- |
| m-Anisidine | 0.233 | 100 |
| o-Anisidine | 0.057 | 24 |
| p-Anisidine | 0.110 | 47 |
| p-Aminosalicylate | 0.123 | 53 |
| p-Bromoaniline | 0.100 | 43 |
| 4-Aminoantipyrene and indole | 0.113 | 49 |

The slopes were normalized to assign a value of 100% to the slope for m-anisidine. The slopes obtained for the other indicators were then listed as percentages of the slope obtained for m-anisidine. Steeper slopes represent better quantitation. The results summarized in the table show that the difference between the color intensities developed in response to 2% and 5% glucose are substantially greater for m-anisidine than for other indicators. The results show that the slope obtained with m-anisidine was at least twice as great as that obtained with several structurally related and structurally dissimilar redox indicators.

EXAMPLE II

An optimized prototype containing a low concentration of tetramethyl benzidine and m-anisidine was prepared as in Example I using the following ingredients to form a test solution for application to test strips:

| | |
| --- | --- |
| Citrate Buffer, 2.0 M, pH 5.5 | 1.0 ml. |
| Peroxidase, 50 mg./ml. | 2.0 |
| Glucose Oxidase, 5,000 I.U./ml. | 3.0 |
| Polyvinyl Pyrrolidone, 15% in Ethanol | 1.9 |
| Emulphor ON-870, 10% in Ethanol | 0.5 |
| m-Anisidine | 0.112 |
| Tetramethyl Benzidine, 0.05 M in Tetrahydrofuran | 0.5 |
| Tetrahydrofuran | 1.0 |
| Total Volume | 10.0 |

The performance of these strips was evaluated with the use of 56 clinical urine specimens. The colors developed by the test strips in response to glucose present in these samples was compared to a standard color chart with blocks equivalent to 0.0, 100, 250, 500, 1,000, 2,000 and 5,000 mg./dl. glucose. The test strips could readily distinguish all these levels. A correlation plot comparing these results with a hexokinase reference procedure provided a linear regression of $y = 1.07\ X + 0.08$ and a correction coefficient of 0.93.

What is claimed is:

1. A method for the semi-quantitative determination of glucose in urine which comprises contacting the urine with a test strip comprising a bibulous carrier matrix bearing the residue left by impregnating it with a liquid reagent solution comprised of a solvent, glucose oxidase, a peroxidatively active substance and m-anisidine with subsequent evaporation of the solvent to leave the dry reagent with the reagent components being present in the carrier matrix in amounts and proportions such that the carrier matrix is capable of differentiating between concentrations of 2,000 and 5,000 milligrams of glucose per deciliter, and determining the amount of glucose present from the color change in the reagent.

2. The method of claim 1 wherein the liquid reagent composition contains from 1,000 to 1,600 international units of glucose oxidase per milliliter, 600 to 1,300 international units of horseradish peroxidase per milliliter and from 10 to 15 milligrams per milliliter of m-anisidine.

3. The method of claim 2 wherein the solution contains from 0.5 to 1.0 milligram per milliliter of a second chromogen having a high extinction coefficient.

4. The method of claim 3 wherein the second chromogen is benzidine, syringaldazine, diaminofluorine or o-tolidine.

5. The method of claim 3 wherein the second chromogen is tetramethylbenzidine.

* * * * *